(12) United States Patent
Spoonhower et al.

(10) Patent No.: US 7,782,189 B2
(45) Date of Patent: Aug. 24, 2010

(54) SYSTEM TO MONITOR THE INGESTION OF MEDICINES

(75) Inventors: John P. Spoonhower, Webster, NY (US); Edward Covannon, Ontario, NY (US)

(73) Assignee: Carestream Health, Inc., Rochester, NY (US)

( * ) Notice: Subject to any disclaimer, the term of this patent is extended or adjusted under 35 U.S.C. 154(b) by 291 days.

(21) Appl. No.: 11/351,140

(22) Filed: Feb. 9, 2006

(65) Prior Publication Data

US 2007/0008113 A1    Jan. 11, 2007

Related U.S. Application Data

(63) Continuation-in-part of application No. 11/156,959, filed on Jun. 20, 2005.

(51) Int. Cl.
*G08B 1/08* (2006.01)
(52) U.S. Cl. .............. 340/539.12; 340/539.13; 340/573.1; 340/573.4; 340/10.1; 340/572.1; 340/572.4; 340/572.7; 340/5.92; 604/59; 604/60; 604/362; 235/385; 235/492; 600/300; 600/301; 600/302; 600/513
(58) Field of Classification Search ............ 340/539.12, 340/539.13, 573.1, 10.1, 572.1, 572.4, 572.7, 340/5.92; 604/362, 59, 60; 235/385, 492; 600/300, 301, 302, 513
See application file for complete search history.

(56) References Cited

U.S. PATENT DOCUMENTS

| | | | |
|---|---|---|---|
| 3,958,066 A | 5/1976 | Imamura et al. | |
| 4,093,709 A | 6/1978 | Choi et al. | |
| 4,309,707 A | 1/1982 | James et al. | |
| 4,707,362 A | 11/1987 | Nuwayser | |
| 4,712,868 A | 12/1987 | Tung et al. | |
| 5,252,962 A * | 10/1993 | Urbas et al. ............ 340/870.17 |
| 5,682,143 A | 10/1997 | Brady et al. | |
| 5,833,603 A * | 11/1998 | Kovacs et al. ............... 600/317 |
| 5,850,196 A | 12/1998 | Mowers | |
| 5,874,099 A | 2/1999 | Dionne et al. | |
| 5,914,381 A | 6/1999 | Terado et al. | |
| 5,923,572 A | 7/1999 | Pollock | |
| 5,963,136 A | 10/1999 | O'Brien | |
| 6,025,780 A | 2/2000 | Bowers et al. | |
| 6,083,523 A | 7/2000 | Dionne et al. | |
| 6,301,364 B1 | 10/2001 | Lowmiller et al. | |
| 6,306,610 B1 | 10/2001 | Bawendi et al. | |
| 6,326,144 B1 | 12/2001 | Bawendi et al. | |
| 6,366,206 B1 * | 4/2002 | Ishikawa et al. ......... 340/573.1 |
| 6,481,857 B2 | 11/2002 | Smith | |
| 6,538,566 B1 | 3/2003 | Morand et al. | |
| 6,700,491 B2 | 3/2004 | Shafer | |
| 6,748,797 B2 | 6/2004 | Breed et al. | |
| 6,765,476 B2 | 7/2004 | Steele et al. | |
| 6,820,314 B2 | 11/2004 | Ferguson et al. | |
| 6,851,615 B2 | 2/2005 | Jones | |
| 6,855,551 B2 | 2/2005 | Bawendi et al. | |
| 6,894,614 B2 | 5/2005 | Eckstein | |
| 6,899,829 B2 | 5/2005 | Shelnut et al. | |
| 7,253,716 B2 * | 8/2007 | Lovoi et al. ............... 340/10.1 |
| 7,504,954 B2 * | 3/2009 | Spaeder .................. 340/573.1 |

(Continued)

*Primary Examiner*—Tai T Nguyen

(57) ABSTRACT

A system for monitoring ingestion of medicine (21) comprises forming a digestible radio frequency identification (RFID) tag (10). The RFID tag is attached to the medicine. The RFID tag and medicine are ingested. A signal from the RFID tag is monitored.

4 Claims, 15 Drawing Sheets

U.S. PATENT DOCUMENTS

2003/0058110 A1   3/2003   Rich
2004/0008123 A1   1/2004   Carrender et al.
2005/0088306 A1   4/2005   Andreasson et al.

* cited by examiner

SYSTEM TO MONITOR THE INGESTION OF MEDICINES

CROSS REFERENCE TO RELATED APPLICATIONS

This is a continuation-in-part of application Ser. No. 11/156,959, filed Jun. 20, 2005.

FIELD OF THE INVENTION

The present intervention relates in general to tracking ingestion of medication, and in particular to detecting proper use of medication using fragile radio frequency identification (RFID) tags.

BACKGROUND OF THE INVENTION

It is desirable to monitor internal bodily events, sometimes over a period of time, without immediate access to medical facilities. For example, the ability to track-medicine ingestion and absorption into the body is useful for verifying proper usage, monitoring drug interactions, controlling dosage and maintaining inventory control.

Traditional methods of obtaining internal physiological information include: physically probing the body via an orifice or incision with tools such as endoscopes or laparoscopes; imaging the body with modalities such as x-ray, computed tomography or magnetic resonance imaging; or collecting biological samples such as blood, saliva, bodily secretions, or biopsy tissue. It would be appealing to probe the living body without the effort, expense, inconvenience and risk of injury or infection involved with the above methods.

An improvement on these traditional means is the use of ingestible cameras, such as the Pillcam™ produced by Given Imaging (see www.pillcam.com). These swallowable cameras in pill format collect images and basic physical measurements such as pH and temperature as they travel through the digestive tract. Pillcam's™ main use is to collect internal images to help with diagnosis of conditions inside the digestive tract. These devices have been proven to provide useful information about the state of a subject without additional invasive medical procedures. However, such cameras are relatively complex, expensive, unpleasant to swallow, and are limited in their ability to collect physiological information.

Radio frequency identification (RFID) tags are a class of device that can also be applied to the problem of tracking internal physiological activities. An RFID tag includes an antenna made of a material that can be caused to sympathetically resonate by a field attuned to a particular frequency (typically in the radio range). The resonance of the antenna in the field in turn becomes a source of information by broadcasting at the resonant frequency. These devices are more flexible in their range of applications, less expensive, simpler and therefore more robust than the solutions discussed above. As shown in FIG. 1, the standard components of an RFID tag 10 include a circuit 12, a resonant cavity 14, and an antenna 16 assembled on a substrate 18 or other means of providing support to the components just stated. Current RFID technology offers many solutions that take advantage of a remote querying capability combined with decreasing cost.

RFID tags have a long history. During World War II the British used RFID tags to remotely distinguish between friendly and hostile approaching aircraft. The World War II VT Fuze manufactured by the Eastman Kodak Company and others emitted a radio signal that responded to the proximity of a metal target by becoming increasingly in phase until the combined strength of the emitted and reflected signals was sufficient to activate the fuze.

Further evolution of the RFID tag occurred when Thermin pioneered the use of passive RF to spy upon the American Embassy in Moscow. The precursor to modern passive RFID tags, an external radio transmission provided power to a resonant circuit at certain frequencies. Certain conditions, such as people speaking in a room, would modify the modulation of the resonance, which would then be received and demodulated, creating an extremely simple and robust wireless means for listening to remote conversations.

More recently, RFID technology has been applied to the medical field in inventions such as affixing RFID tags 10, to containers for medicine 20, shown in FIG. 1, patients, and medicine dispensers, such as IV bottles. These RFID tags can be remotely queried in order to track the medicine usage. (See U.S. Patent Application Publication Nos. 2005/0088306 A1 (Andreasson et al.) and 2004/0008123 A1 (Carrender et al.). One major shortcoming of this approach is that the RFID tag is on the container and not in the medicine that is ingested. Although usage can be tracked, a method that verifies ingestion and digestion of medicine by a specific person cannot be implemented.

Although potentially useful, another approach is to provide RFID tags that can be implanted in a living body without fear of breakdown or interaction. U.S. Patent Application Publication No. 2003/0058110 A1 (Rich) refers to an RFID system that can be embedded under the patient's skin. However, RFID tags that require implantation in the human body for monitoring biological activity and medicine delivery will also require removal when no longer needed, a near certainty for most conditions needing medicinal treatment. Permanently implanted devices and tags require engineering and construction to attempt to preclude damage and failure as is taught in U.S. Pat. Nos. 6,083,523, 5,874,099 (both to Dionne et al.), and others by Dionne et al. and may be cost prohibitive for the majority of the patient population. Simple systems of permanent RFID tags embedded under the skin have been developed for tracking and identifying pets such as disclosed in U.S. Pat. No. 5,850,196 (Mowers) Finally, in cases where the RFID tag is meant to pass through the body, as the Pillcam™ does, engineering is required to ensure that the RFID tag circuit is not damaged in the process of ingestion and elimination, again potentially increasing the cost and size of the device.

Therefore a need exists for a system to accurately monitor a patient's ingestion and digestion of medicine, without the use of permanently embedded equipment or cost prohibitive RFID solutions.

SUMMARY OF THE INVENTION

The need is met in the present invention by the incorporation of fragile RFID tags into medicine. Briefly, according to one aspect of the present invention a system for monitoring ingestion of medicine comprises forming a fragile (which means destroyed by interactions within and with the body and therefore not requiring removal because it has been digested or otherwise assimilated) radio frequency identification (RFID) tag. The fragile RFID tag is introduced into the body by being attached to the ingested medicine or by being otherwise embedded in the body. Once inside the body, the fragile RFID tag's signal is monitored.

Although radio frequency is the most often referred to wavelength in teaching this invention, this invention teaches embodiments that use other wavelengths and fields for remotely communicating with the fragile tag.

A fragile RFID tag contains an antenna made of a material that can be caused to sympathetically resonate by a field attuned to a particular frequency (typically in the radio range). In this respect, the fragile RFID tag is similar and well understood to all previous art on creating tags that can be remotely queried such as U.S. Pat. No. 5,682,143 (Brady et al.) and U.S. Pat. No. 6,894,614 (Eckstein et al.). The resonance of the antenna in the field in turn becomes a source of information by broadcasting at the resonant frequency. Normally such antennae are created of metals or biologically inactive metals such as gold in small amounts such as in the form of a thin foil. When a pill is ingested, the antenna structure is destroyed over a period of time by the body. Other forms of edible and conductive materials such as encapsulated metallic liquids, clays (such as Silly Putty) or even liquids or gases can also be used to create a suitably fragile antenna that would be destroyed in the process of consumption without harming the consumer. These materials, having been previously passed over for use precisely because of the their fragility and lack of robustness, are ingestible because of the small amounts that would actually be consumed since such ingestible conductive materials need not comprise the whole of the device, but need only be used in sufficient quantities and areas so that the function of the tag is comprised upon consumption. The need for RFID tags that can be deactivated is touched on by U.S. Pat. No. 6,025,780 (Bowers et al.) when they teach a means of disabling a RFID tag, but they do not seek to design a tag that is engineered to self-disable.

A home environment or a medical kiosk would have at least one constant RF source (such as those in use to detect RFID payment information in gas stations) that would recognize existence or nonexistence of an antenna. By having a plurality of RF sources, the 3D location of each antenna can be determined. With a system to monitor the kind, existence and location of each medicine the following devices and services become possible:

The lockable drug dispenser (who is attempting to take medicine; what they took; preventing overdosing or reminding the patient to take medicine)

A kiosk/bathroom attachment that insures the medicine is taken on the spot (keeps the door locked until the medicine is taken)

A means of determining if the medicine was taken or dropped down a toilet or sink A means of reminding the patient which medicine to take by tracking the medicine taking history A means of sharing the medicine taking history with medical staff A means of guarding against medical interactions with food, vitamins, and other medicines by using a medical tracking history This invention is a system that uses intentionally fragile tags to provide useful information by identifying when such tags are destroyed or rendered inoperative. The system then responds to this basic change of state by providing a useful service. Such intentionally fragile tags can be composed of materials that not only can be ingested but also digested with the understanding that break down is a desirable quality and one that enables the tag materials to be eliminated in the standard manner. Such a fragile tag that is also digestible lends itself to applications such as being included in objects meant to be ingested, such as pills, lozenges, and glycol strips.

Applications favored by such a system include tracking medicine, not by container but the medicine itself; and tracking the medicine to its destruction by the body. Such a capability in turn enables systems that automatically dispense drugs with the ability to insure that the drug is taken on the premises otherwise exiting the premises can be curtailed. When combined with a means of uniquely identifying the medicine taker, the systems can track the frequency and dosage of the medicines taken and can be enabled to automatically limit or increase the dosages on the basis of direct observation or to call for assistance on the basis of medicine taking behavior.

An additional application is where the fragile tag is engineered to breakdown only in the presence of certain compounds, such as, but not limited to, those found in the stomach. Such a system allows convenient and simple to administer drug testing. Such a system also allows convenient sample testing, for example, a urinalysis where the fragile tag is thrown into a toilet and the results are immediately remotely gathered and stored, thus eliminating the need for carrying around a sample.

In another application, the fragile tag is engineered to breakdown under mechanical stresses rather than by chemical reaction. Such a tag may be affixed to an artificial, or natural body part. It is then implanted and can be remotely queried. When wear on the body part, for example, an artificial hip, has proceeded to a predetermined level, the tag is rendered useless thus alerting the remote query that the body part has achieved an unsatisfactory level of wear.

Although the preferred embodiment describes a system utilizing radio frequency identification tags, it should be noted that the simplicity of the system allows for the use of acoustical frequency identification tags, as well as tags that reflect or resonate in other frequencies. Because existence or non-existence provides sufficient information to enable operation of the system, applications can be imagined where the circuitry required in typical RFID tag systems is not required.

The preferred embodiment uses passive tags, but active tags can be of equal or greater use in some instances. The preferred embodiment refers to a single tag but the invention encompasses the use of multiple tags that react in parallel. Multiple tags may be packaged so they are exposed to conditions in a serial manner, over time. Another embodiment uses multiple tags whose packaging yields useful information from some combination of the tags being destroyed or surviving conditions, such as when compounds in the stomach destroy some tags but leave others.

The invention encompasses the extraction of data when conditions partially destroy or otherwise modify a tag. The tag may additionally be composed of compounds such as quantum dots, providing the added functionality that when the tag is ingested, it breaks down into components that can still be tracked by other means.

The invention includes the potential of being externally powered, for example, an RF circuit and the device uses this power to activate or otherwise alter either a circuit that will release or restrict the release of medicine in the body or that will alter the medicine itself to render it active or inactive.

The invention and its objects and advantages will become more apparent in the detailed description of the preferred embodiment presented below.

DETAILED DESCRIPTION OF THE INVENTION

The present invention will be directed in particular to elements forming part of, or in cooperation more directly with the apparatus in accordance with the present invention. It is to be understood that elements not specifically shown or described may take various forms well known to those skilled in the art.

Figure 1:
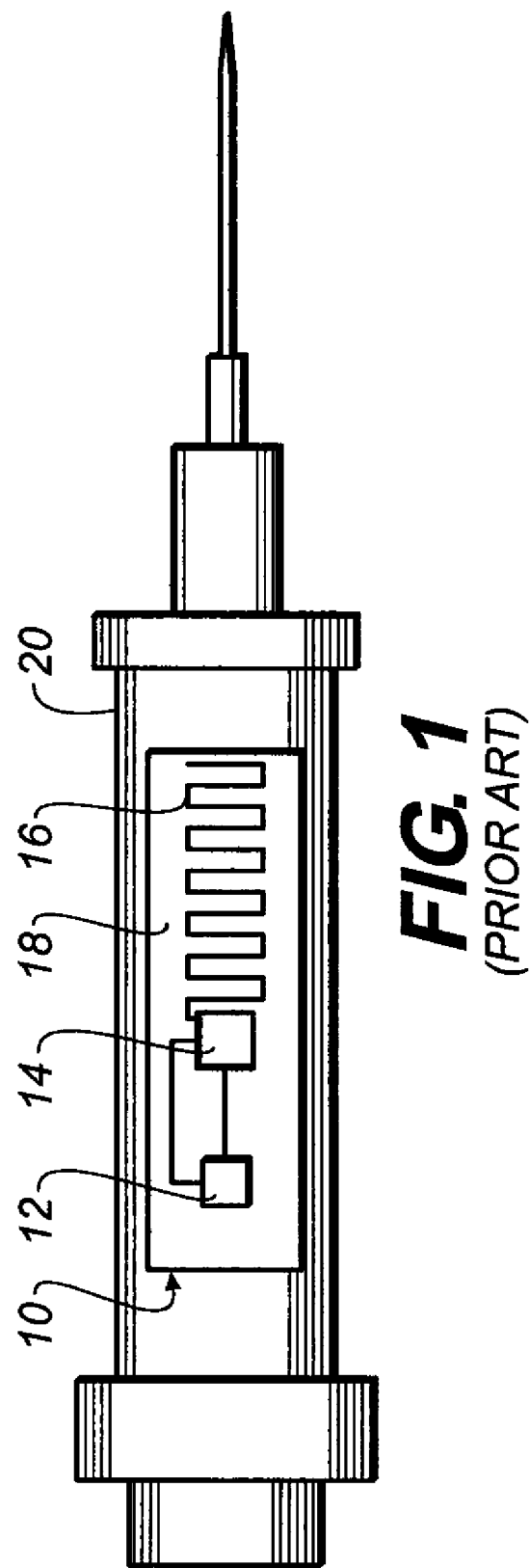
FIG. 1 is a schematic drawing showing a tagged medicine container and a radio frequency identification (RFID) tag.
Figure 2:
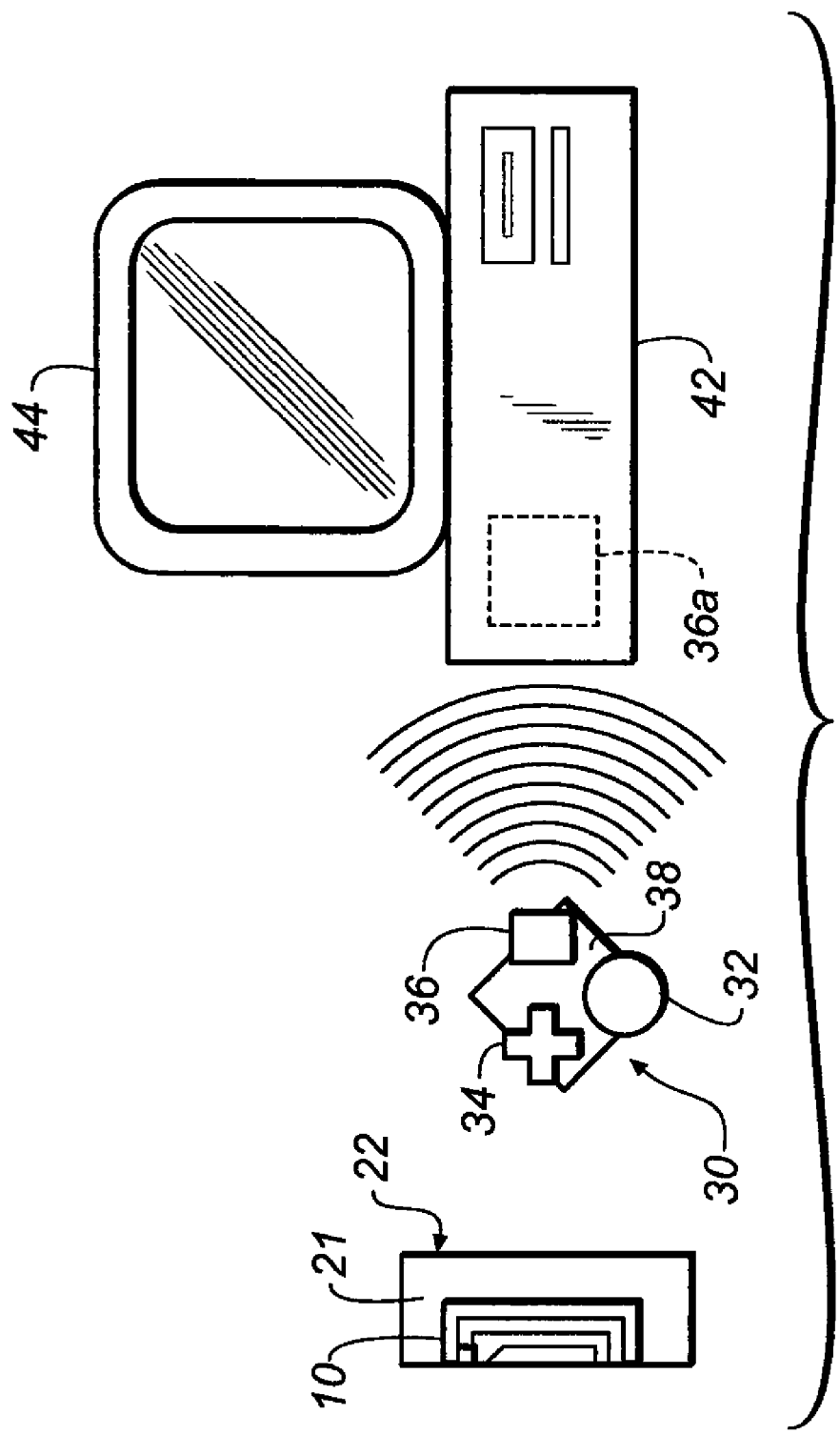
FIG. 2 shows components of system for monitoring the ingestion of a fragile RFID tagged medicine.

Referring now to FIG. 2, a system for monitoring ingestion of tagged medicine 22 is shown. A digestible radio frequency identification (RFID) 10 tag is carried by (that is, affixed to or embedded in) medicine 21 to form tagged medicine 22. When ingested, tagged medicine 22 is detected by a monitoring device 30.

Monitoring device 30 is comprised of a storage device 32, an emitter 34, and a transceiver 36. These components are attached to a support 38 which may be worn as a belt or otherwise affixed to a person's body.

Information from the monitoring device 30 may be transmitted to a transceiver 36a, which is connected to a computer 42. Information received from the monitoring device 30 is viewed on monitor 44.

Figure 3:
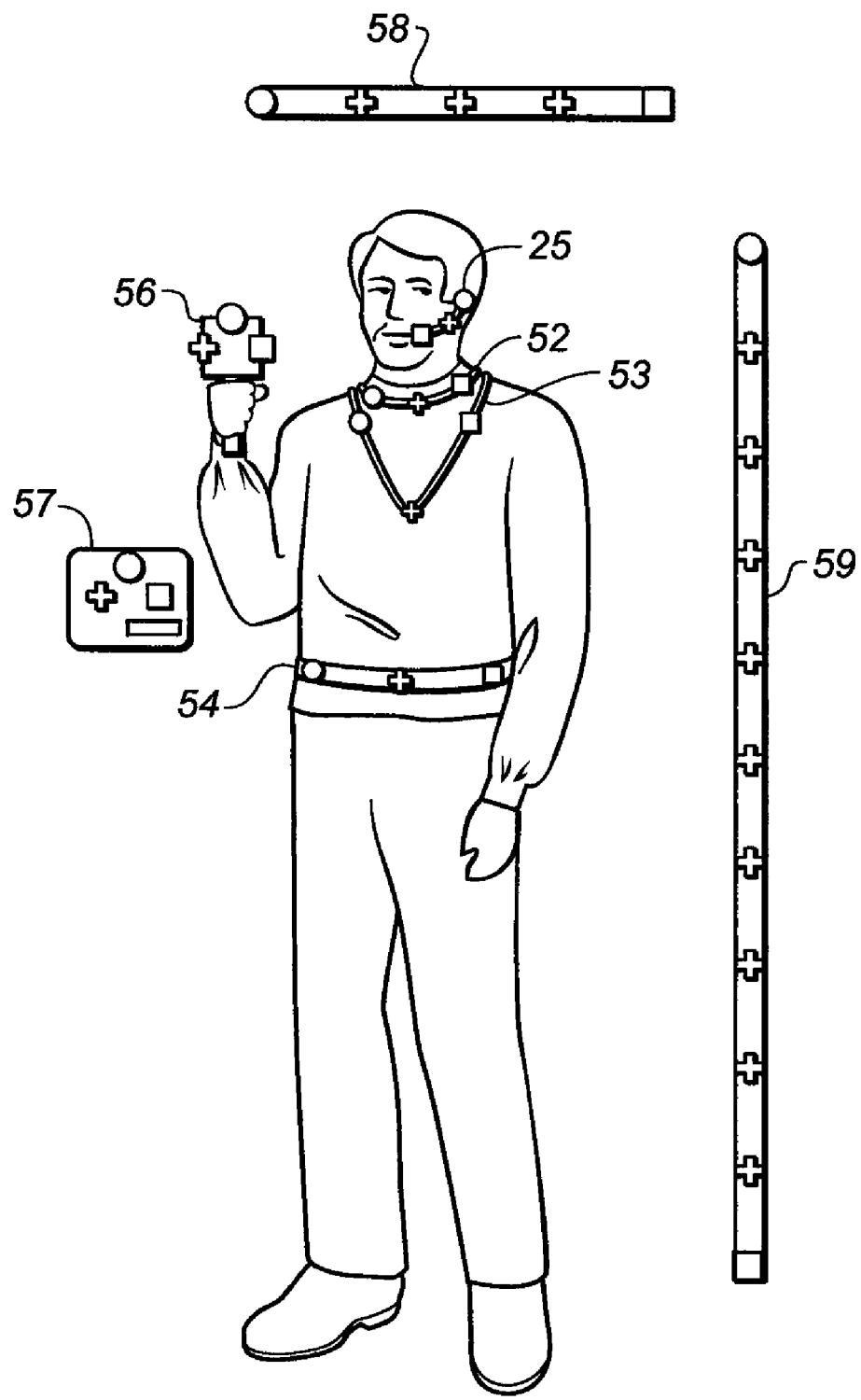
FIG. 3 is an illustration showing variations of monitor placement for the system.

Referring to FIG. 3, monitoring device 30 may be incorporated in different articles to be worn on the body. Some examples include collar 52, lanyard 53, and belt 54. Monitoring device 30 may also be located in close proximity to the mouth, for example on an earpiece and boom 25. Monitoring device 30 may also be incorporated in handheld devices 56, medicine dispensers 57, overhead apparatus 58, or wall mounted apparatus 59.

In all cases, the monitoring device would function similarly. When tagged medicine is ingested, an external RF emitter sends a signal that travels through the body and causes a resonance in the RFID tag as discussed above. Thus, the travel of the medicine through the body can be tracked at any point desired. For example, if the collar 52 is worn, the medicine can be detected as it is swallowed. If the belt 54 is worn, the medicine can be detected as it enters the stomach. And both of these examples, the monitoring device can also detect when the tagged medicine has passed these points, as well as detecting when the medicine has entered these points.

Figure 4:
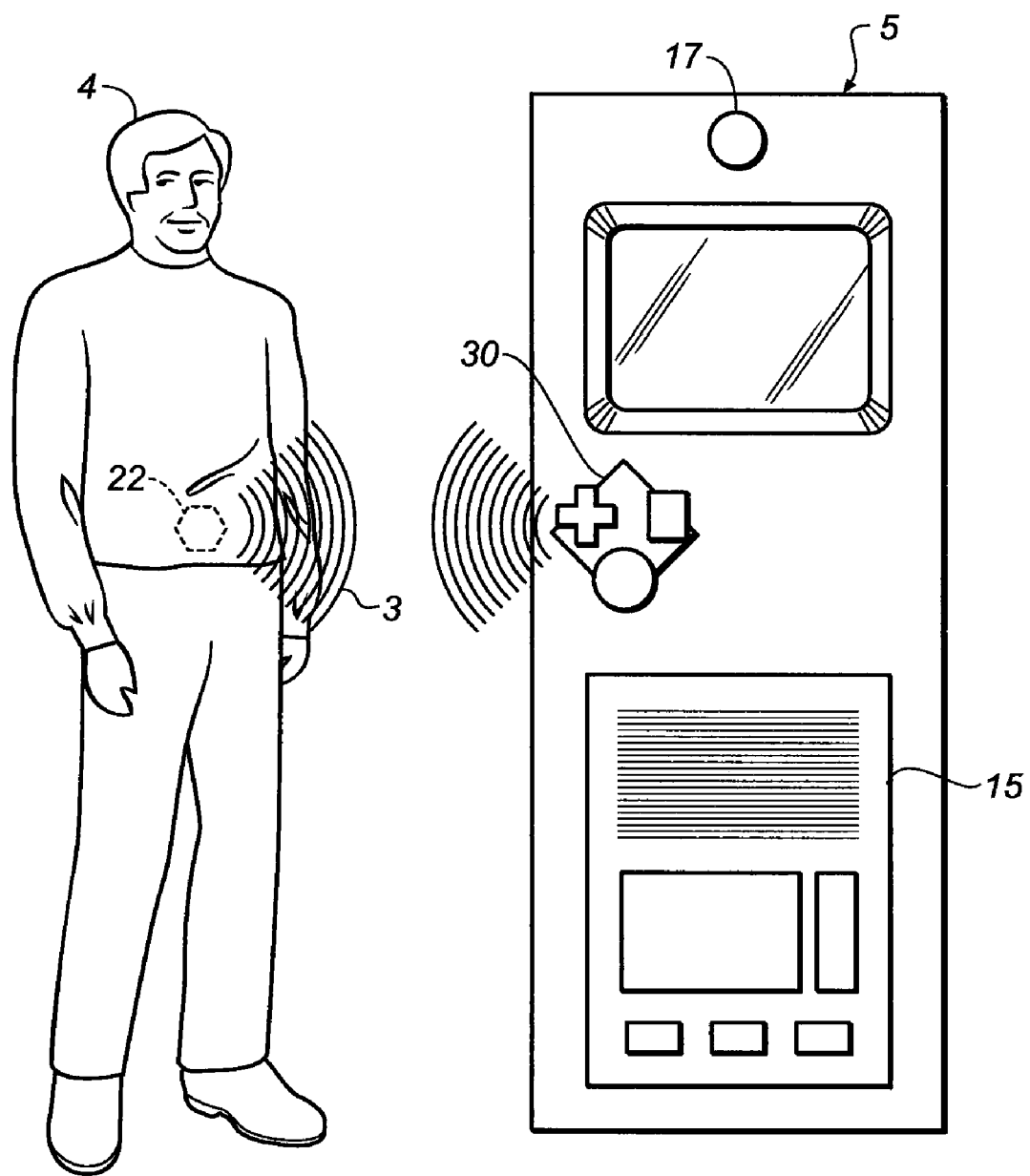
FIG. 4 is an illustration of a kiosk version of the system.

The concept can also be applied to environments other than that of a stand-alone system. FIG. 4 shows how this can be applied at a medical kiosk. A medical kiosk is a device that performs tests and checks on a person, for example, blood pressure, weight, blood oxygen levels, strep tests and others. The kiosk can have personal assistance, be unassisted or have a remote video links for assistance. With a fragile RFID tag that can detect specific drugs or controlled substances, a kiosk can be utilized to test prescription or illegal drugs in person's bloodstream. In this case, the tag will activate when in contact with the specific drug or substance of interest.

A subject 4 walks up to a medical kiosk 5. A fragile RFID 22 is dispensed and ingested. Ingestion can occur by the medicine and substance or drug-specific RFID tag being incorporated into a skin patch applied by the subject. Upon contact with the substance of interest, a signal 3 is sent from the tag and is picked up by a monitoring device 30 within the medical kiosk 5. A proximity detector 17 is utilized to ensure that the subject 4 is within proper distance for the signal 3 to be detected by the monitoring device sensor 30 in the medical kiosk 5. The information (ingestion, detection, or both) is recorded by the kiosk computer 15, stored, printed, and or transmitted to a location of interest (doctor, supervisor, caregiver or the like).

Potential applications for this include illegal drug testing in government and certain sporting situations (some observation would be required to make certain the tag is applied or ingested and by the proper test subject). It could also be used in a elder care facility to determine the level of prescription drugs that a subject was expected to be ingesting and to monitor the actual ingestion of prescription drugs to get to the proper levels. Other application areas are those where the subjects may be difficult to deal with in the taking of medications or other ingested materials (perhaps even a location sensor to positively identify who and where a person is). Examples are school children, military personnel, prisoners and even pets.

Figure 5:
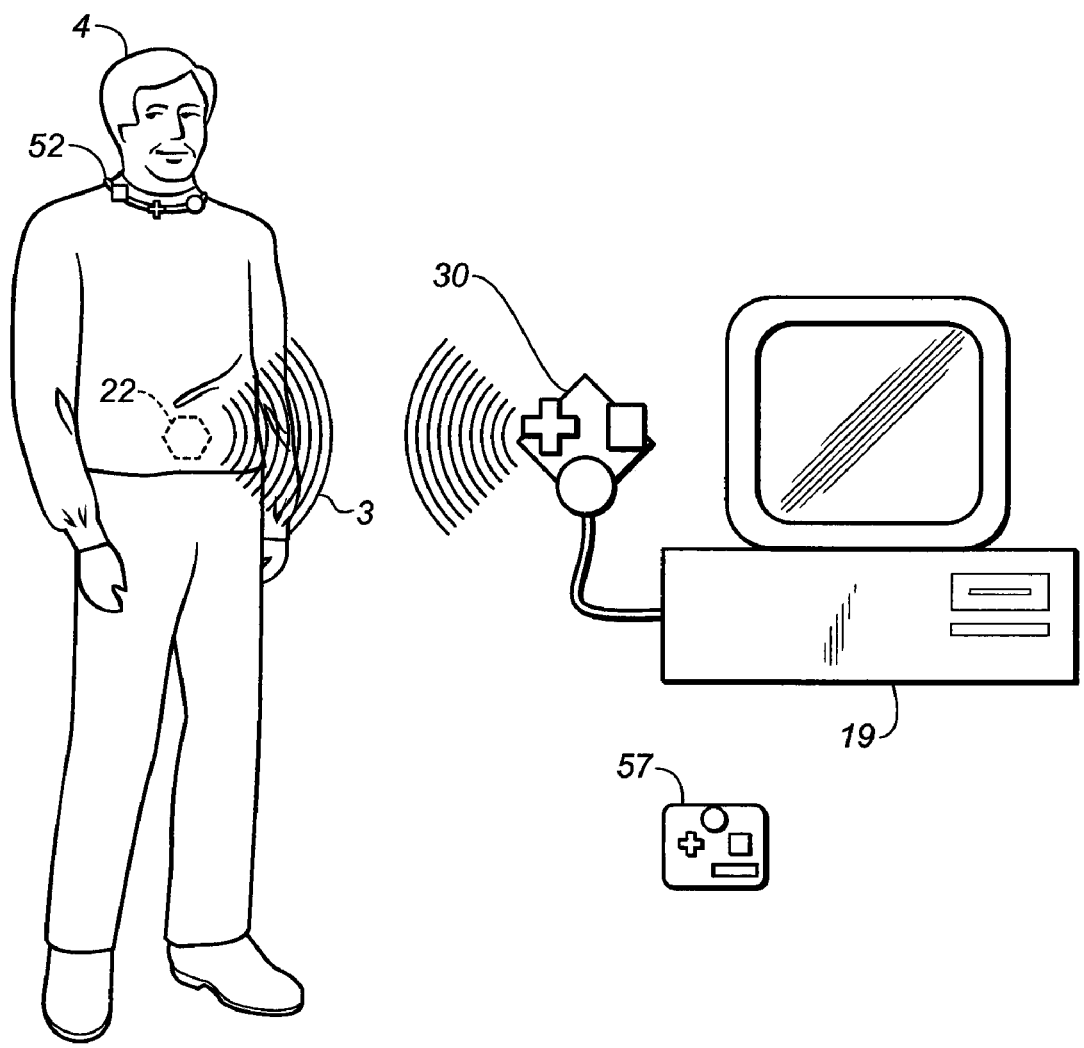
FIG. 5 is an illustration of a home version of the system.

FIG. 5 shows an implementation of the fragile RFID using a home system. Examples of application areas here include homebound individuals where a doctor or nurse needs to be informed of the proper ingestion of medications and the dosages that are being taken. Cardiac care patients, the elderly, those who must take many medications, people with memory problems or those in remote locations are examples of subjects. In this embodiment, a device is attached to a typical home computer 19. Monitoring device 30 is a combination sensor and proximity detector that connects through one of the standard communication interfaces on the home computer 19. This interface can be a USB, RS-232, or wireless connection and software that can determine if the subject 4 is within the proper distance for the sensor to be able to detect the signal from the RFID tag 22 as well as the detection itself. When the tag is ingested, the signal 3 (either that the ingestion has occurred or it contact with a substance of interest has been detected) is sent out and picked up by the monitor 30. The signal (or lack of such) is then recorded, using the aforementioned software and stored on the home computer 19 or transmitted to another location, such as a doctor's office, a nursing station, caregiver, or other persons of interest.

Another embodiment that applies to FIG. 5 is that of a computer on wheels (COW) that are often found in hospitals. The same monitoring device 30 can be added here and a similar scenario will follow as for a home PC. In addition, portable computers, laptops, tablet PCs, Pocket PCs and even personal digital assistants (PDAs) can be utilized as long as a monitoring device can be utilized. Since most of these devices have wireless capability, this poses little problem.

A medicine dispenser 57 can also be part of this system and used to keep track of the medicines as they are dispensed. This information can be compared with the ingestion of the medicines to determine if they have been ingested as intended. The detail is explained later in FIG. 8.

Figure 6:
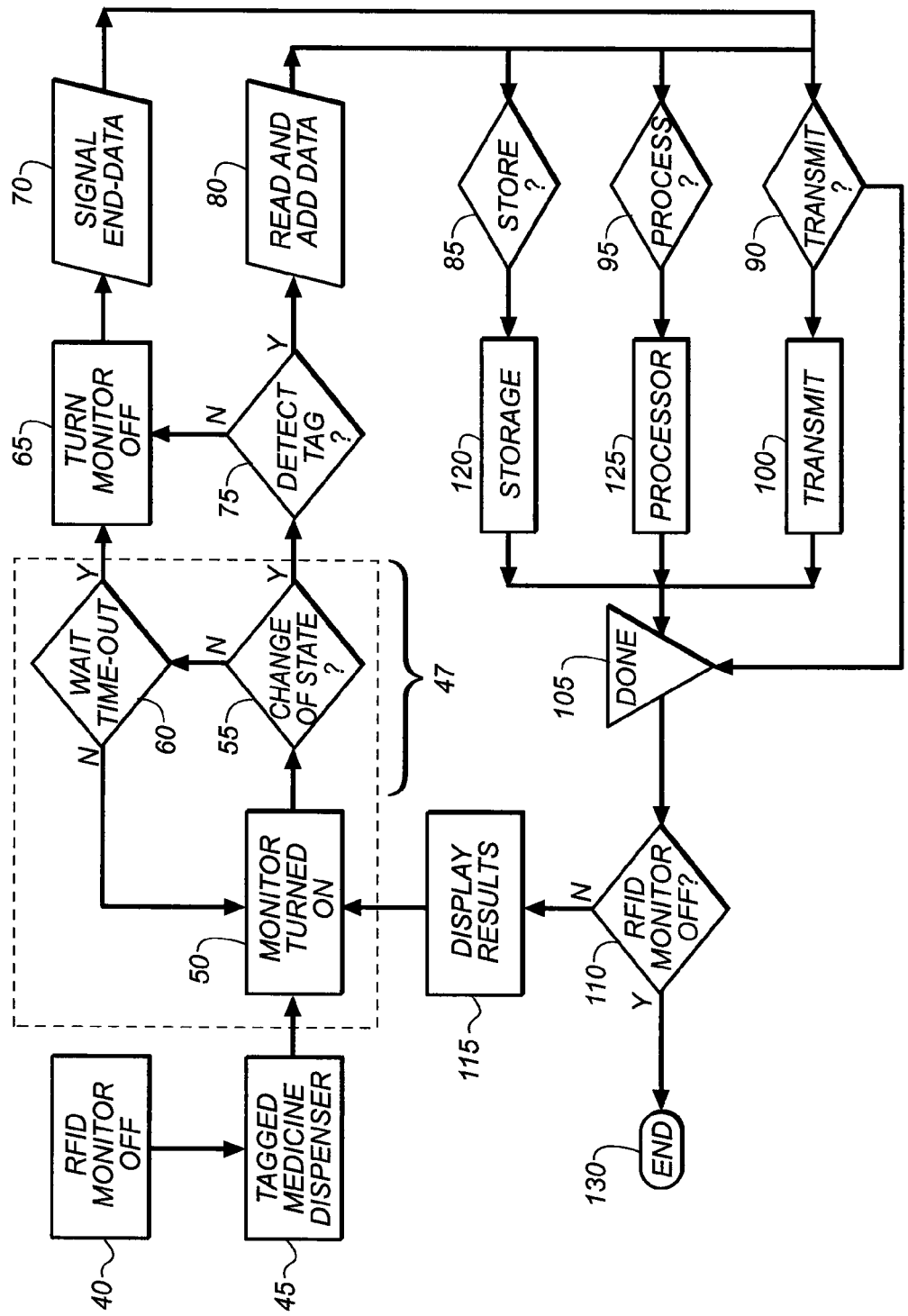
FIG. 6 is a schematic drawing showing the flowchart for a sequence of events according to the present invention.

FIG. 6 shows a sequence of events appropriate to the present invention. The patient's monitor is initially in an "off" state 40 since it is assumed that there is little benefit to having the monitor continuously on (although there may be case exceptions where there is a need to do so). Taking the medicine will involve opening or otherwise manipulating a medicine dispenser 45 which will then send a signal that activates the patient's monitor 50. The process then goes into a loop 47 waiting for the detector's state to change 55 because it has detected the existence of the tagged medicine. It is reasonable to assume that if no medicine is detected or if the tagged medicine is not destroyed within some predetermined time limit, that the system will cease waiting and time-out 60 resulting in exiting the loop by turning off the monitor 65 and signal an appropriate (no tagged medicine or no tagged medicine destroyed) incomplete end-data 70. For example, when a person opens (or otherwise activates) the medicine dispenser 45 but does not take the medicine, the time of the false event and the medicine involved should be recorded and sent to a caregiver or other involved in monitoring the patient's well being as related to medicine use. It should be noted that the patient and the caregiver may be one and the same person.

FIG. 6 further diagrams how after the tagged medicine has been sensed 75 by the monitor, the data such as the identification and dosage of the medicine is read from the tag and combined 80 with other data such as time of day by the system of this invention. The data then can be stored 85, transmitted 90, or be additionally processed 95 as desired by the users of the system. For example, a caregiver may wish to be immediately notified of the act of the patient taking a particular medicine so the system is enabled to send a transmission 100 which may be the only step so that the system function is done 105 and since the monitor "off" check is failed since finds the monitor "on" 110, the results are displayed 115 for the caregiver. The caregiver may also wish to have a record of the medicine taken for later comparison against other vital signs and aspects of change in the patient's health so storage 120 would then also be enabled. Finally, the caregiver may wish to compare the time, dosage and identification of the medicine against rules for taking the medicine so additional processing 125 of the data would also be done. It is likely that all three steps would be done since the result of processing 125 the data would likely lead to the need to transmit 100 an alarm (a form of display in the understanding of this patent) if certain rules were violated and for the actions to be stored 120 for later reference.

Upon completion of the desired steps related to verifying taking the medicine, that is when all the initial tasks required of the system are done 105, the system confirms that the medicine is in fact taken by continuing to loop 47 through the process until the time-out limit is exceeded 60 or until the tagged medicine is destroyed causing a change of state 55 which in turns fails the tag existence check 75 which results in the monitor being turned off 65 and the which causes the process to signal an end-data 70 which is followed by the steps mentioned of checking whether transmission 100, storage 120 or additional processing 125 is enabled for the time out or tagged medicine destruction step. This final pass through the system encounters the monitor "off" check 110, and upon passing goes to the end state 130. It should be noted that inventions such as U.S. Pat. No. 5,963,136 (O'Brien), and recently U.S. Pat. No. 6,851,615 (Jones) and others anticipate the need and appropriateness of using RFID tags for managing medicine and medicine dispensers, but such inventions do not use a process that seeks and is able to validate that the proper dosage has been take.

A special case exists when the fragile tag is designed to exist for a longer duration, such as when there is a need to indicate something other than immediate ingestion and consumption of a medicine. An example of such a need is wear of an internal structure such as bone at a joint or an implanted device such as a pacemaker, artificial joint, or similar device. Unlike the process in FIG. 6, the process begins when a fragile tag attached to a device or the fragile tag itself is surgically otherwise embedded in the body. Therefore the step of the tagged medicine being dispensed 45 is eliminated and the process begins with the monitor being turned "on" through some other process, manual or some other automated trigger (presenting a unique identifier such as a card with data encrypted upon the card in some media, biometric data such as facial recognition, or some additional form of tagging for identification purposes) rather than a step of automatically turning the monitor "on" 50 as described in FIG. 6. At subsequent times, the monitoring process keeps looping 47 (albeit in loops of longer chronological duration then those waiting for the fragile tagged medicine to be destroyed) and checking continues until the fragile tag is destroyed 55. The monitoring process can be manual using a handheld scanner, automatic wherein the patients present themselves to a scanning device built into a kiosk or semiautomatic where human observation is combined with a mass screening system. When the tag ceases to exist the monitor sends the end data 70 described in FIG. 6 to the system and the appropriate actions are taken.

Figure 7:
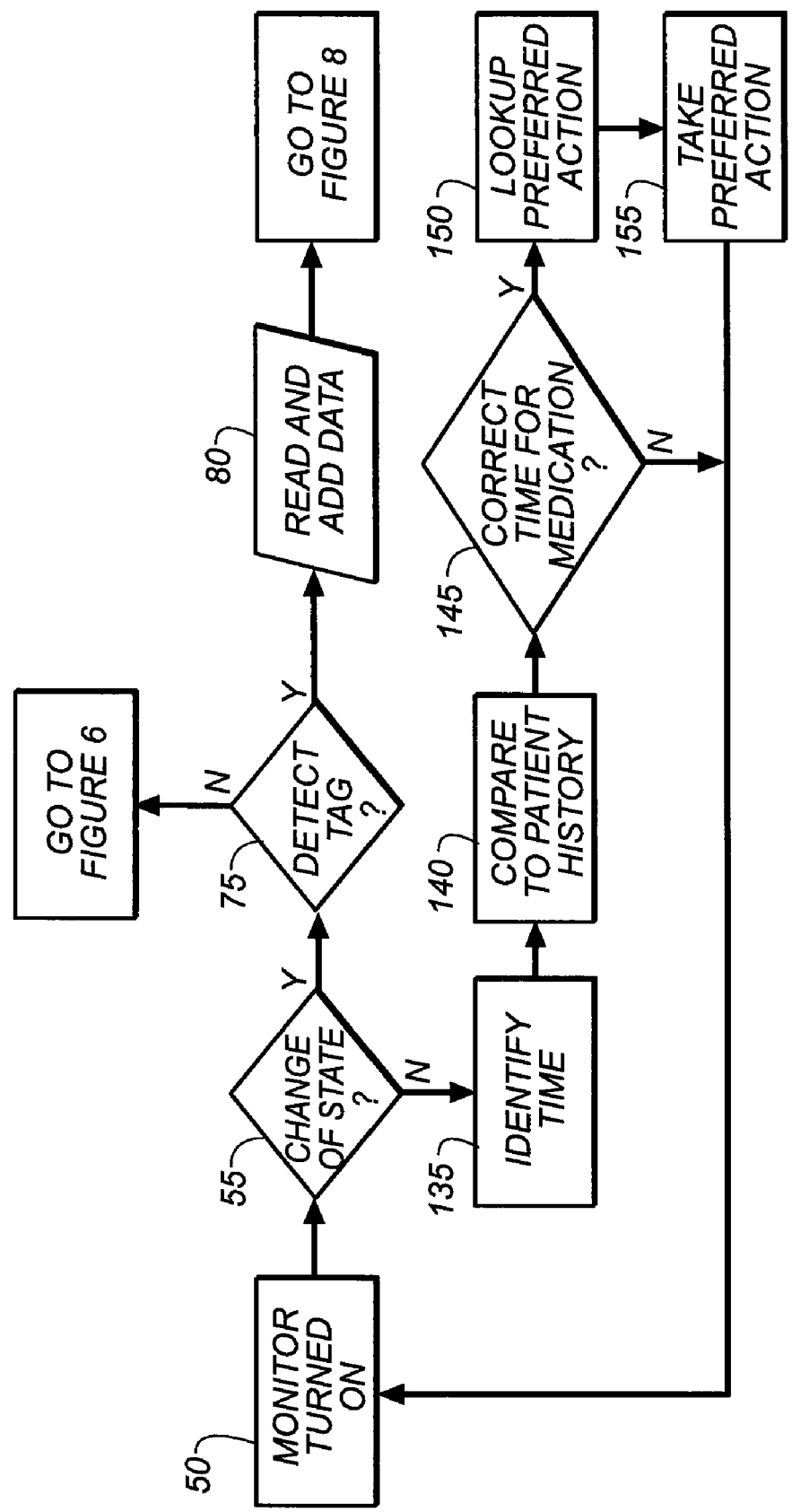
FIG. 7 is a flowchart of the system of the present invention processing information utilizing negative feedback.

FIG. 7 provides a flowchart of representative processing steps for a more complex set of responses to the negative feedback loop of the sort described in FIG. 6 as a general timing out loop 47 in the sequence of events comprising the invention and which is not meant to be all-inclusive. Unlike FIG. 6, FIG. 7 clarifies a case where the system is constantly monitoring for the intake and/or destruction of the fragile tagged medicine. The loop 47 may respond with an additional loop based on negative feedback information (such as "no fragile tagged medicine has been detected") by constantly looping where each loop results in checking for a change of state 55. When there is no change, each loop additionally checks the time 135. The current time when checked 135 may then be compared to the patient history 140 to establish a relative time to some prior event (such as the taking of some other medicine, time prior to sleep or time since having dinner) as opposed to a simple absolute passage of time as previously referred to in FIG. 6 in step 60 as checking for a time out. A comparison of relative time can be used to decide on whether it is the correct time to take medication 145 such data can be compared to a database containing other time information such as an absolute time for a particular medication to be taken as referred to in FIG. 6. This also provides a means to check on the longitudinal consistency of proper and timely ingestion. Upon comparison and determination if the medicine should be taken 145 the system can (if it is time to take the medicine) proceed to looking up a preferred action 150 and then executing the action 155; as opposed to FIG. 6 where the only action referred to was turning off the monitor 65 and signaling end of data 70. A preferred action in this case may be a response such as turning on an audiovisual alarm that medicine needs to be taken. Prompts other than time are also readily considered and familiar to those versed in the art of monitoring the state of a patient's condition relative to the need of the patient to take medicine.

Figure 8:
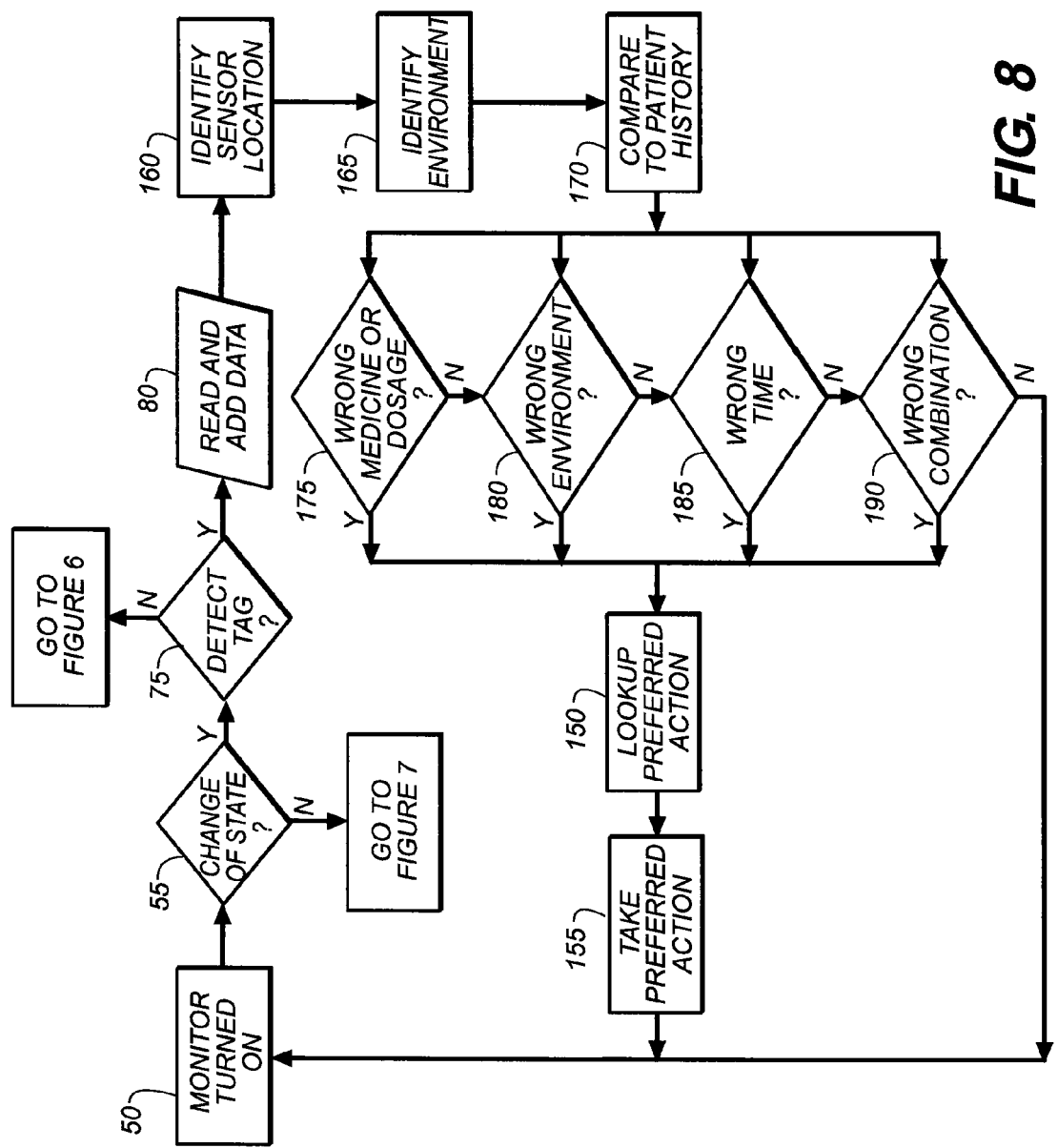
FIG. 8 is a flowchart of the system of the present invention processing information utilizing positive feedback.

FIG. 8 continues the flowchart begun in FIGS. 6 and 7 representing a more complex loop 47 sequence of events. FIG. 8 represents a positive feedback component to the loop 47 where information, specifically, the test "has there been a change of state" 55 is passed and triggers a positive loop. Under conditions where the fragile tagged medicine has been detected as being taken and/or destroyed and information has been received from the fragile tag, and read 80, the step of reading and adding data 80 is followed by additional specific steps such as the identification and thus, knowledge of location of a particular sensor 160 and/or group of sensors and this information combined by the system with environmental information 165 such as (but not limited to) time. Other potential forms of environmental and personal data that might be of use are temperature, light levels, position or posture of the patient, temperature of the patient, pallor, chemical balance of the blood, heart rate, oxygen levels and all other forms of patient information known to practitioners of the medical arts. By comparing such data to the larger patient history 170 useful conclusions about the impact of taking the medicine can be drawn. As an example, a computerized system can compare the medication and dosage prescribed to the medication and dosage being taken and identify an error in dosage 175 and issue an alarm if such is the preferred action 155, if there is an error. Similarly, the system can be programmed to recognize appropriate aspects of the environment 180 such as the patient attempting to take a "photodynamic" drug such as sulfonamides, tetracyclines, sulfonylureas, thiazide diuretics, or nalidixic acid, where under sunlit conditions, such a drug would react adversely to sunlight. Another condition is based on the comparison to absolute and relative times 185 for the medicine to be taken, particularly in conjunction with the proper circumstances and environment 180. For example, the patient should be not be taking the medicine too soon after eating. Routinely, it is important to be aware of what medicine was taken when in order to avoid taking an improper combination of medicines 190 being taken. The system can in each case lookup 150 a preferred action and, if so enabled, execute 155 the preferred action as a more complex variation on the option listed in FIG. 6 of simply displaying the data.

It should be noted that the following illustrations are not meant to and do not provide accurate scales and sizes, and are instead meant to illustrate the basic functional relationship of the components.

Figure 9:
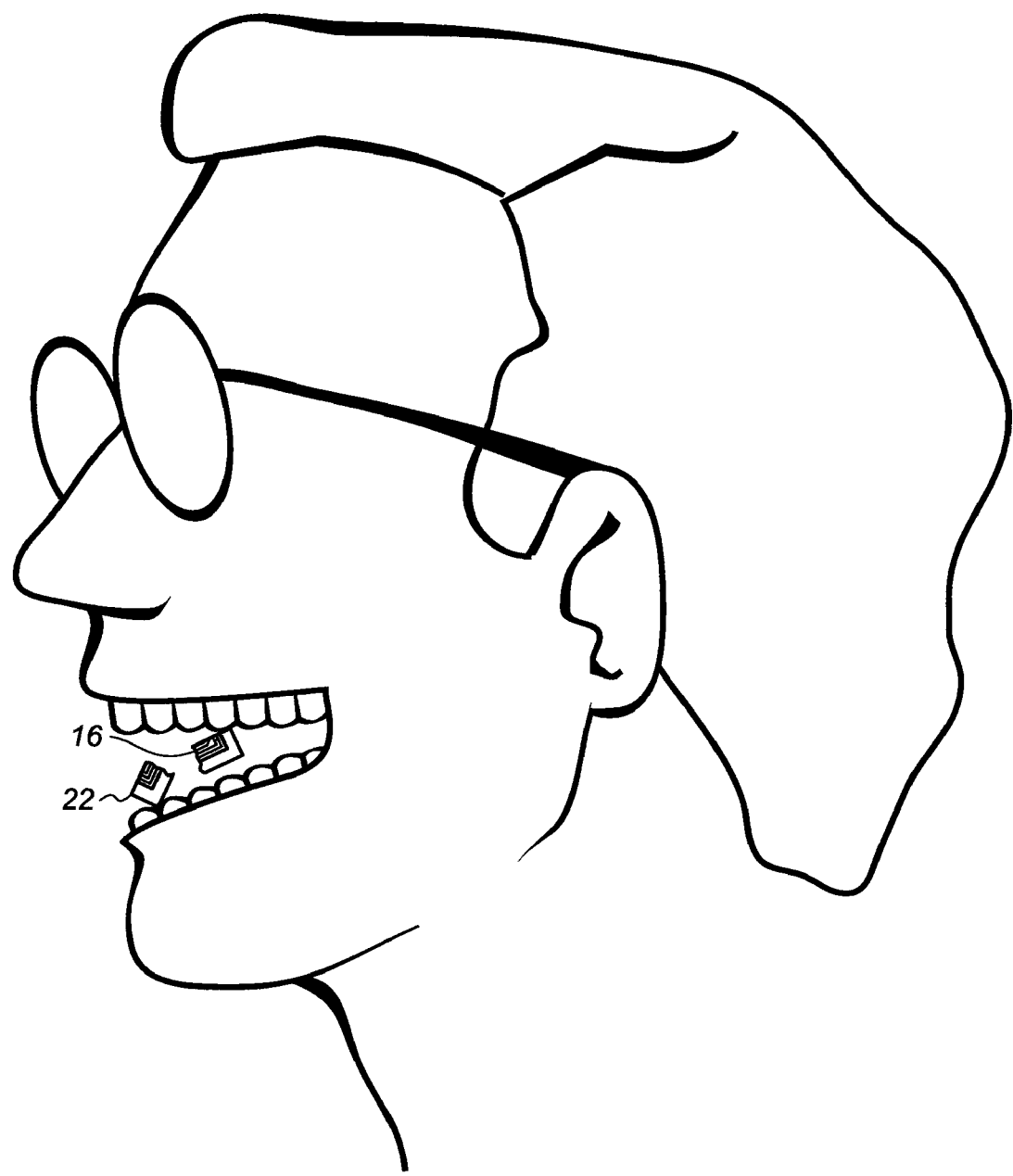
FIG. 9 is an illustration if a fragile RFID tag being destroyed in the mouth.

FIG. 9 schematically suggests that a fragile RFID tag 22 can be useful even if it does nothing more than cease to respond when chewed. In this example, the RFID tag antenna 16 is assumed to be made of a consumable material that also acts as a good antenna, such as copper. Silver, gold, or conductive polymers such as such as those taught in U.S. Pat. No. 6,899,829 (Shelnut et al.) and many others going back to U.S. Pat. No. 3,958,066 (Imamura et al.) and earlier are also suitable, including those noted by Shelnut's teaching being such colloidal compositions as have a selectivity for non-conductive surfaces. It should be noted that RFID antennas can be made of very thin films, in fact printed tags for mail use are in the range of net tag thickness of 0.0008 inches as taught by U.S. Pat. No. 6,820,314 (Ferguson et al.), and still function allowing for some latitude in the choice of materials for the antenna. In this example, the medicine is assumed to be in the form of chewable lozenge or a glycol strip such as those manufactured under the Listerine brand and other mouth antiseptic products such as Listerine Pocketpaks™ as found at www.oral-care.com. Designing for fragility requires that the ductility of metal (if metal is used), or pliability of the conductive polymer, tolerates handling but is not so great that the antenna or the packaging interferes with its destruction when taken. As stated in the description for FIG. 3, a monitor mounted on a boom 25 or other structure or otherwise affixed to the skin inside or outside the mouth or embedded in a tooth then responds to presence and then the absence of the functioning fragile RFID tag as previously discussed in FIG. 6.

Figure 10:
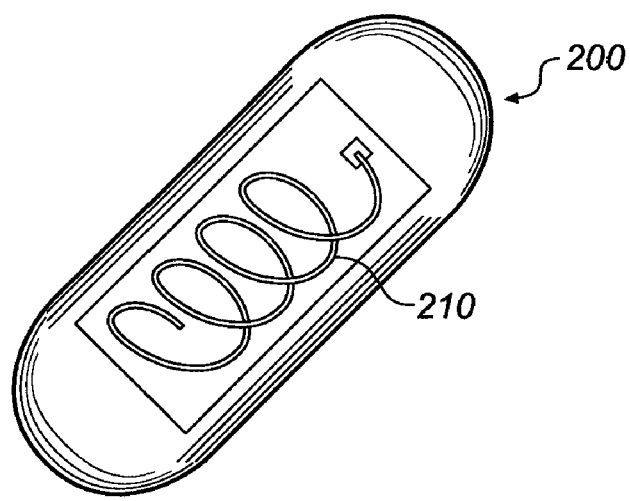
FIG. 10 is an illustration of a fragile RFID tag suspended in a capsule.

FIG. 10 illustrates a fragile RFID tagged capsule 200 with the antenna formed in a helical shape (or other appropriate three dimensional figure) as is well known in the art and as typically taught in U.S. Pat. No. 4,309,707 (James et al.), specifically that the antenna is not in a flattened form factor but the antenna is in a three-dimensional coil 210, allowing compact encapsulation. The fragile RFID tag is then encapsulated in a manner familiar to those versed in the art of manufacturing capsules of medicine. The gelatin coating typical of such capsules (or degradable polymer as taught by U.S. Pat. No. 5,914,381 (Terado et al.) or other suitable coating) would dissolve in the standard manner in the mouth or stomach allowing the fragile antenna to be destroyed in accordance with the process outline in FIG. 6.

Figure 11:
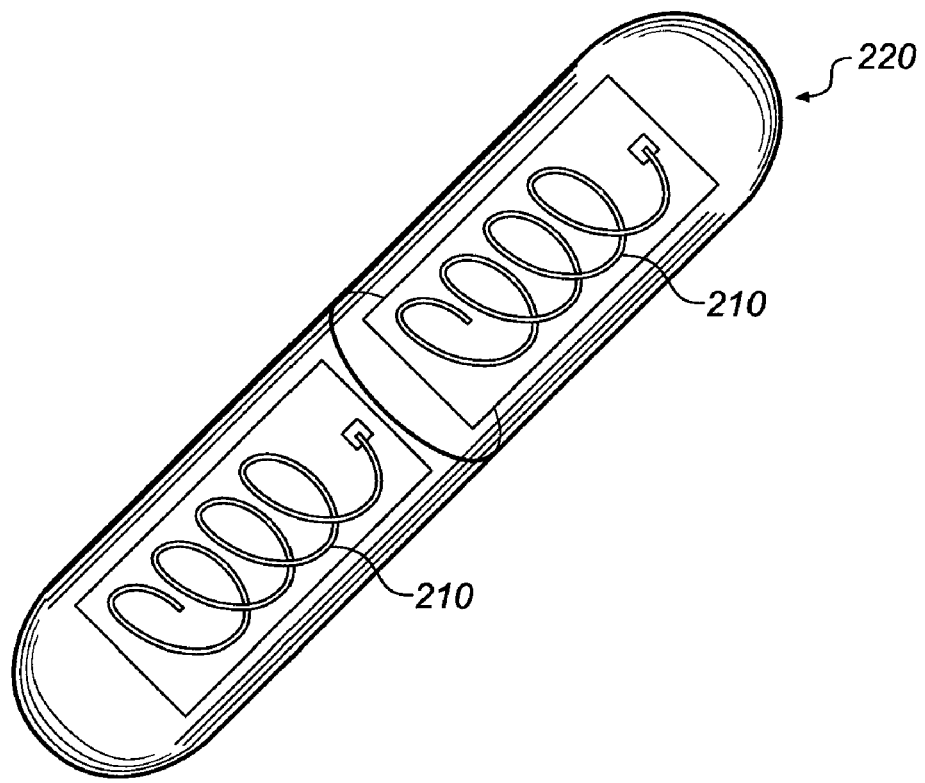
FIG. 11 is an illustration of a compound fragile RFID tag.

FIG. 11 illustrates a compound capsule 220 where more than one fragile RFID tag is encapsulated. Each fragile tag is encapsulated in a different substance, or in the same substance but where the substance has been treated to react differently to its environment. So, capsule 220 is constructed in different ways to resist dissolution to a varying degree. The same substance is varied in thickness or textured as is evident to the least gifted in the art of packaging medicine. When biodegradable time-release medicaments as specified in U.S. Pat. No. 4,093,709 (Choi et al.) are used, the same microspheres can be packed around the different fragile RFID tags. The use of more than one capsule 220 for encapsulating more than one tag and having such additional capsules linked in a single dose permits testing for compounds as well as identifying rates of absorption. Multiple tags can interfere with each other when responding to an RF source, so that the destruction of one or more tags would reveal its identity by process of elimination since the remaining fragile tag could then be clearly identified providing potentially useful information. Alternatively, the fragile RFID tag may be surrounded by micro-spheres of medicine that interfere with the RF signal much like a Faraday cage, in which case the fragile RFID tag would be detected by the monitor for a limited time between the dissolution of the surrounding materials and the dissolution of the fragile RFID tag. Additionally, subcarriers may be used as taught by U.S. Pat. No. 6,765,476 (Steele et al.) as well as other schemes that allows the use of multiple RFID tags antenna in close proximity to another by adjusting the use of monitors and antennas.

Compounds typical of those used to coat ingested capsules with different types of reactivity to the environment found within the body are listed in patents found by searching time and release and medicine such as U.S. Pat. No. 4,707,362 (Nuwayser).

Figure 12A:
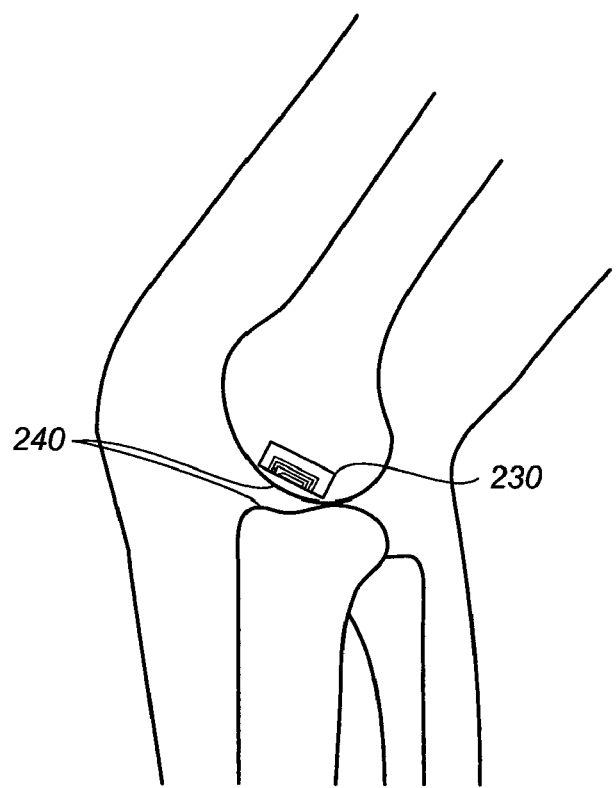
FIG. 12a is an illustration of a fragile RFID tag that is fragile because it is embedded to show mechanical wear at a joint.

FIG. 12a illustrates the use of a fragile RFID tag whose value is derived from mechanical wear of the tag 230. This example of use refers back to the special case mentioned at the end of the description of FIG. 6 where the fragile tag is embedded in the body rather than ingested. A clearly appropriate application for such an embedded fragile tag is as part of a protective layer on top of bone 240 or other surface or body part that experiences wear. In the case of bone, the wear is due to mechanical friction as well chemical reaction. In either case, there is value in ascertaining the breakdown of the surface of bone or of an artificial or natural bone replacement. As described in FIG. 11, there would be value in compound fragile tags but in this case such multiple fragile tags would be separated by location rather than substance in a capsule so as to allow assessment of where wear is occurring as well as degree of wear in order to assess the impact of movement in which the patient typically engages. Additionally, since the antenna of the fragile RFID tag is required for acquiring the RF power, design of the antenna so that wear degrades the functionality of the fragile tag's antenna (by shortening its length) prior to complete failure may be an appealing feature in some applications. Additional advantage comes from using the motion of the tag relative to a worn monitor to identify and record motion (to warn the patient of inappropriate or excessive motion) as taught in the related case of tire motion by U.S. Pat. No. 6,748,797 (Breed et al.) and U.S. Pat. No. 6,538,566 (Morand et al.) until such time as the tag is worn away.

Figure 12B:
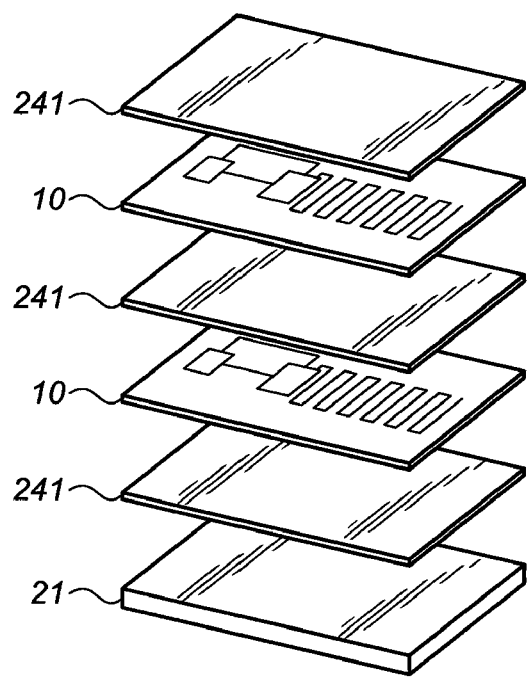
FIG. 12b shows an additional form of fragile RFID tag where multiple layers of RF blocking material are used.

FIG. 12b illustrates in greater detail the concept that the fragile tag can be designed so it is enabled by a worsening condition before it is destroyed. By interposing an RF blocking layers 241 between the fragile RFID tags 10 and the medicine 21 thus completely blocking the tags to external resonance, the fragile RFID tag would indicate a worsening condition first by being inactive, then active, then (in a terminal condition) by being again inactive as it is destroyed. Such blocking layers can be composed of any radio frequency blocking (in the case of the fragile RFID tag) or other wavelength blocking or dampening material as appropriate. Typical of such blocking materials would be a Faraday cage composed of a fine weave of gold wire, a foil of such blocking material (and others that have the property of conductance and being capable of safe ingestion.) By using multiple fragile RFID tags and layers, increasing amounts of specific wear and related information can be extrapolated.

An additional feature is the possible use of the embedded tag to monitor internal vibration in much the same manner as the Thermin listening device referred to in the background. Such vibration monitoring devices, functioning as a miniature stethoscope, can be remotely queried as originally used by Thermin in his U.S. Moscow embassy listening device.

It should be noted that fragile tags may not only be embedded surgically, but may be embedded by shooting or jabbing the body to insert the fragile RFID tag, thereby providing a safe and convenient method for testing the state of a body of a person or animal that would otherwise not cooperate in such test. An example of such an application would be an uncooperative animal that needs to be tested by a veterinarian or tagging an animal in the wild.

Other embodiments of mechanical interaction could be a fragile tag whose fragility is derived from response to external pressure. A typical application for such a fragile tag would be where following being embedded, such a fragile tag would function until a loss of blood pressure below a set limit occurred at which point the tag would be destroyed, giving an immediate indication of the metabolic state of the recipient of the fragile tag. Similar applications can be extrapolated for loss of air pressure in the lungs.

Other embodiments of mechanical interaction could further include a fragile tag that fails when temperature exceeds a certain limit. Compound fragile tags of this type could provide a rapid means of remotely and automatically monitoring internal body temperature.

An embodiment that combines aspects of mechanical and chemical fragility is the bio-reactive fragile tag. A casing, substrate, or component of the fragile tag would be designed to support the growth of a specific mold, fungus, bacteria or virus. The destruction of the fragile tag would then indicate the presence of the organism.

Not illustrated, but mentioned, is the means of using multiple circuits connected to a single antenna such that wear will successively disable one identification circuit (by breaking a connector) while enabling another (by breaking a barrier).

Surgically imbedded fragile RFID tags are not limited to attachment to bone or artificial implants to check for wear. They may also be attached to medication that is designed for slow release over a long period of time. For example, a pellet of medication implanted at a tumor site may incorporate a fragile RFID tag to detect the rate of release of the medication from the pellet, or the exhaustion of the medication.

Figure 13:
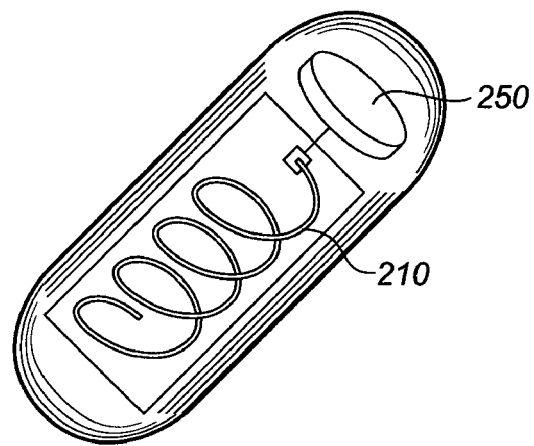
FIG. 13 is an illustration of an active fragile tag.

FIG. 13 illustrates an alternate embodiment of the concept of valuable fragility in medical tagging. In this case the tag 210 is not passively deriving its power from sympathetically resonating to an external RF source, but instead is powered by either an internal power source 250 in the capsule (as shown in the figure) such as a battery or a battery that is also an antenna as taught by U.S. Pat. No. 6,700,491 (Shafer) or device for extracting power available from its environment through means other than RF broadcast. The desirability of this more complex and expensive variant rests in the value of being able to dispense with the antenna and the external application of power, allowing passive monitoring systems. It should be noted that the value of fragility for such a device continues since the same functional value is provided by tracking its structured breakdown (as well as adding the feature that it does not need to be retrieved.)

The capsule may contain a power source, like the given "Pillcam," or a means of extracting power from the environment. Means of extracting power from the environment can be external fields such as a magnetic fields, acoustic stimulation, body heat, mechanical motion converted to energy such as piezoelectrics, or chemical reactions with substances in the body. However, unlike products such as the Pillcam, the capsule would be composed of or contain fragile tag components, such as "designed for failure" elements of the circuit as mentioned with reference to FIG. 12b, that would affect the output of the capsule. As mentioned with reference to FIGS. 11 and 12a, selective breakdown of parts of the circuit could alter the identification signal emitted by the capsule thus allowing creation of a "single use" ingested monitoring system.

It should again be noted that the signal emitted by the capsule does not have to be in the RF range, but may acoustical, in the optical or other part of the wavelength spectrum.

Figure 14:
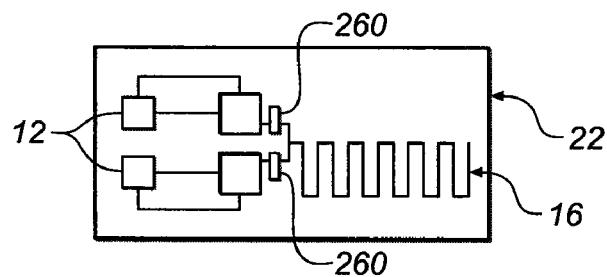
FIG. 14 is an illustration of a fragile RFID tag whose resonance characteristic change due to breakdown in a circuit designed to be fragile.

FIG. 14 illustrates an additional (beyond antenna breakdown) form of fragility useful for identifying the existence of specific compounds. The illustration depicts a device where multiple ID circuits 12 of the RFID tag are connected to a single antenna 16 for transmission by means of connectors 260 composed of reactive compounds such as the aforementioned gold conductive traces that are left exposed to the environment that result in the signal defined by the circuit being altered by the reaction with the surroundings. Compounds such as metals and metallic polymers can function by dissolving rapidly (in essence, cutting the trace to one circuit), and preferentially acting as a form of transistor by enabling the electrical flow or responding to the environment in a micromechanical manner (equivalent to opening or closing a switch). Examples of this function would be where the protective layer is varies by thickness so that one (or more traces) is "cut" before another or where the protective material is chosen such that a specific compound in the in vivo environment causes it to dissolve and expose the reactive material of the trace.

In keeping with the teaching with reference to FIG. 13, not illustrated but easily anticipated, is the use of some power source 250 other than an RF antenna 16 and the connectors 260 functioning by enabling the circuit power from such power source 250 in addition to or instead of the connection to the RF antenna 16.

It should be noted that the external RF monitor that provides power to the fragile RFID tag circuit, could be used to do work. An example is the use of the monitor to initiate a breakdown of the fragile tag (through acoustic vibration or RF radiation and heat) with such breakdown resulting in the breakdown of a barrier that keeps the contents of the capsule from mixing with the environment or breakdown of the antenna. Another mechanism for such a release would be the case of micromechanical release, where the failure of the fragile tag eliminates the source of power to micromechanical device that is acting as a gate which then causes the release of an agent such as a medicine through direct action (the failure of the fragile tag to keep closed a path to an internal reservoir of an agent) or through external mediation where the failure of the tag is monitored and triggers an external device which automatically inject an active agent into the body or where the external device turns on a field or source of radiation that activates a component already within the body.

Figure 15:
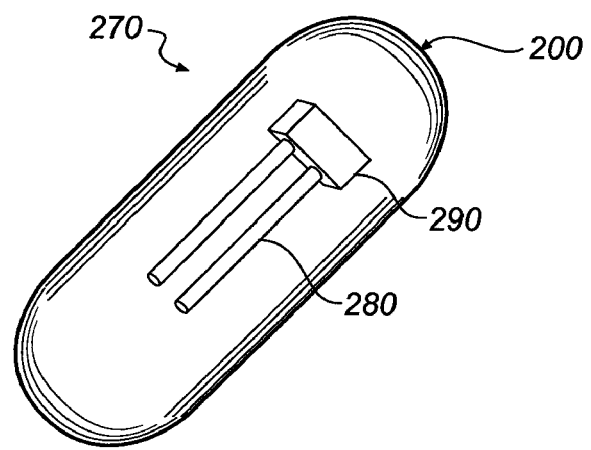
FIG. 15 is an illustration of a fragile identification tag using acoustical properties.

FIG. 15 illustrates a fragile tag designed to respond to external acoustical stimulation 270 (not be confused with "acoustic tags" which are audio signals combined with low frequency noise for the purpose of identification. See U.S. Pat. No. 6,301,364 (Lowmiller et al.)). Since the essential functionality of the fragile tag begins with echoing a generic signal, circuit-less sympathetic resonance can be used to achieve the aims of this invention. This illustration suggests the concept by schematically depicting a device such as a tuning fork structure 280 embedded in the base 290 and placed in a capsule filled with liquid. When the capsule disintegrates so does the tuning fork indicating completion of the medicine taking process. This embodiment benefits from the fact that acoustically resonant materials are routinely organic and found in nature and thus materials such as fibrous substances suitable for ingestion are readily found.

Not shown but easily anticipated by the teaching in FIG. 15 is the use of acoustically resonant voids and spaces in the substance of medicine (regardless of the material being a tablet, capsule, lozenge or other form so long as the medicine has a sufficiently rigid structure). Also not show but easily anticipated by FIG. 15 is the use of resonant threads or strings under tension.

Figure 16A:
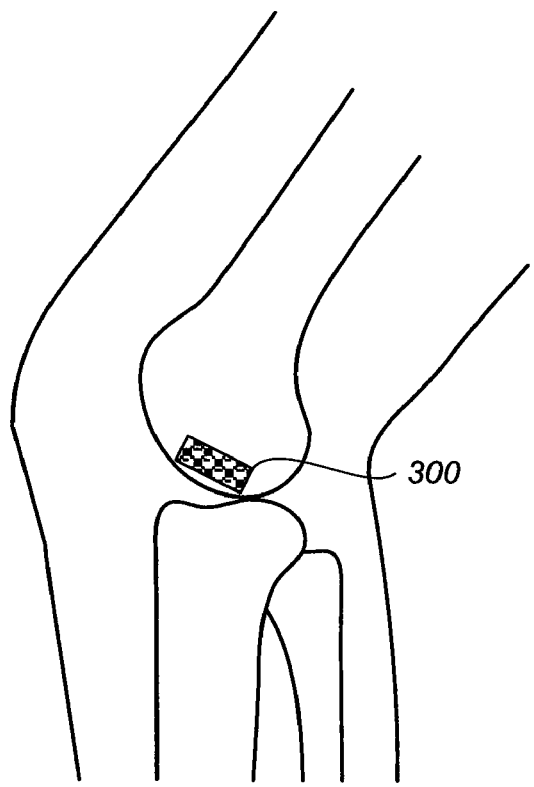
FIGS. 16A and 16B are illustrations of a fragile retro-reflective identification tag.
Figure 16B:
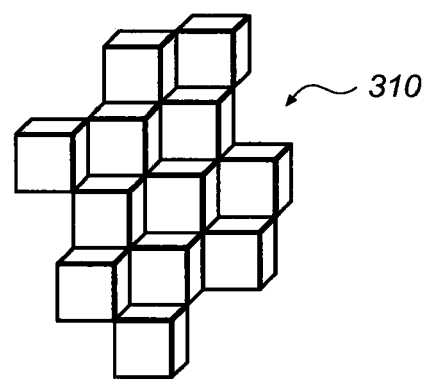

FIG. 16A illustrates use of an embedded fragile tag 300 designed to operate with an external infrared (or acoustic or optical wavelength) source. The infrared reflective tag is located sufficiently close to the surface of the skin that an infrared, terahertz, optical or acoustic laser source tuned to the proper frequency will reflect off the surface tag in a manner that can be externally monitored. To enhance the strength of the reflection, the fragile tag should be in the form of retro-reflective or cube-corner material 310, shown in FIG. 16B, such as that recently taught by U.S. Pat. No. 6,481,857 (Smith) and going back to U.S. Pat. No. 4,712,868 (Tung et al.) and others, yet earlier, to improve the strength of the returning signal. The fragile IR tag would lose reflectivity as it degrades. In addition, different parts of the tag could be coated be different reactive coatings so that in addition to mechanical wear, chemical reaction could be monitored over time.

Figure 17:
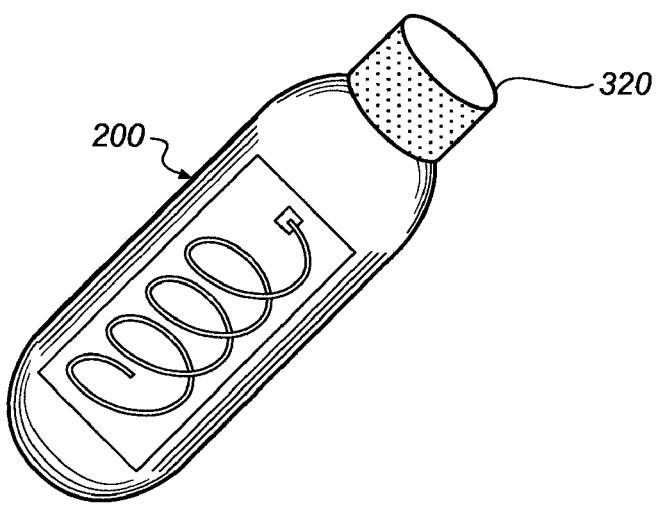
FIG. 17 is an illustration showing the combination of a fragile identification tag and non-fragile components such as quantum dots.

FIG. 17 illustrates the option of combining fragile tags with robust components such as quantum dots 320. As previously mentioned in description of FIG. 13, fragile tags may be combined with components such as transmitters, circuits, mechanical components, micromechanical components and self-contained power sources that are not themselves fragile. Hybrid forms of the device can be exercised in other fashions such as combining any of the fragile embodiments mentioned so far with robust (as opposed to fragile) components and robust markers such as quantum dots, Cornell dots, or related compound release systems. Quantum Dots and Cornell Dots used for biomarkers are discussed by C. Henry in "Quantum Dot Advances" found in the Chemical and Engineering News, Vol. 81, No. 23 (Jun. 9, 2003) p. 10. Another form of hybrid system may be used where an embedded tag identifying the person is used, in conjunction with the monitors worn by the person, to add an additional level of assurance that the proper dosage is being reviewed by the intended recipient without tampering. See U.S. Pat. No. 5,923,572 (Pollock) wherein an embedded tag process is suggested for use in refueling automobiles (but without the aspect of a fragile RFID tag).

In this figure, the use of a reservoir of quantum dots 320 is illustrated. Quantum dots (as well as Cornell dots and similar functional nanomaterials) are designed respond to UV light in a particular fluorescent range such that when the tag itself disintegrates, the quantum dot material composing the tag is released to spread through the body where it is eventually accessible to external monitoring. See U.S. Pat. Nos. 6,855,551; 6,326,144; and 6,306,610 (all to Bawendi et al.), which shows a combination of fluorescent light in the proper frequency with a properly tuned monitor (sensor).

It should be noted that compound fragile tags connected with quantum dot reservoirs 320 of different colors may be advantage since the sequence of breakdown or absence of breakdown of the medicine would provide useful information concerning the rate of dissemination of the marker as the quantum dots (in different colors) are released at different times for external monitoring.

Finally, it should be noted that although embodiments of this invention have been discussed in terms of the in-vitro advantages of using a system that takes advantage of the intentional fragility of the tag, it does not exclude ex-vitro embodiments since these may be found useful and convenient. The same tag that can react to internal bodily chemical states is equally useful in checking bodily excretions, thus allowing the creation of testing systems with a disposable reactive component for testing feces, urine, blood, and all other manner of excretions with an improved level of safety and convenience. For example, the fragile RFID tag may be dropped in the toilet after urination to check for the presence of certain chemicals, without taking the urine sample to a lab for analysis.

Figure 18A:
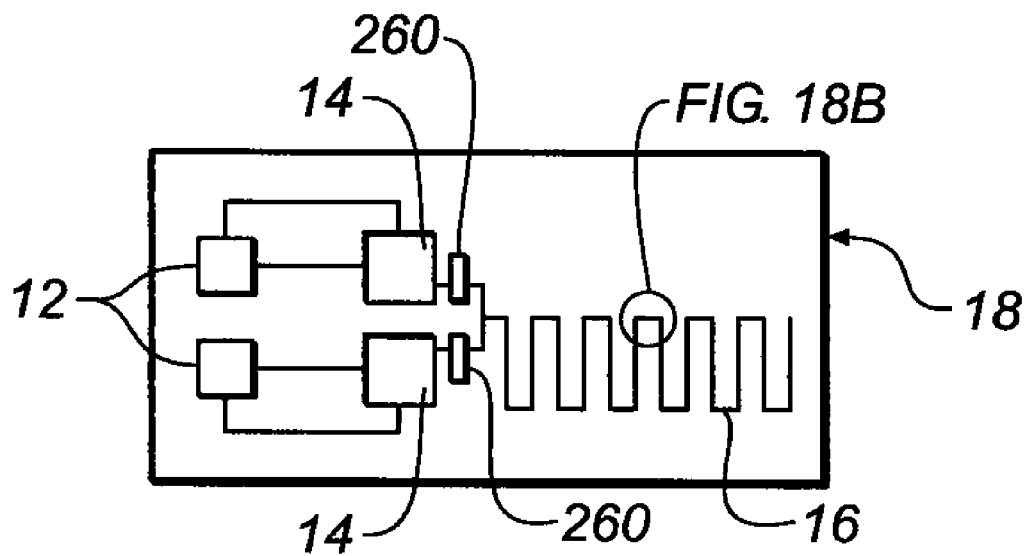
FIG. 18A is an illustration of a fragile RFID tag whose resonance characteristics change due to breakdown in an antenna designed to be fragile.
Figure 18B:
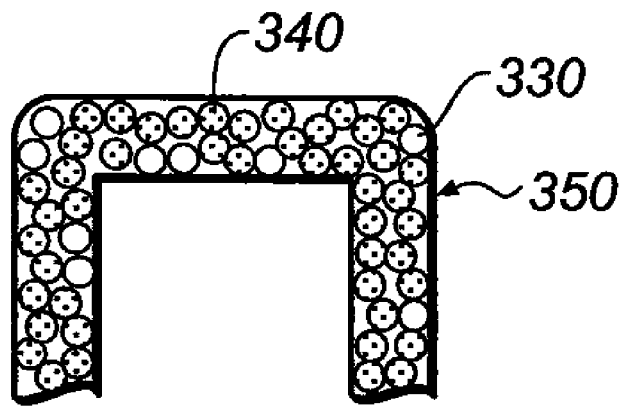
FIG. 18B is an expanded view illustration of an RFID antenna segment of a fragile RFID tag whose resonance characteristics change due to breakdown in an antenna designed to be fragile.

FIG. 18A is an illustration of a fragile RFID tag whose resonance characteristic change due to breakdown in an antenna 16. FIG. 18B is an expanded view illustration of a an RFID antenna segment 350. Referring to both FIGS. 18A and 18B, the RFID antenna 16 is comprised of both conductive particles 340 and non-conductive particles 330. Fragility of the structure results from the dispersal of these conductive particles when digestion occurs. Before ingestion, the conductive particles 340 of the RFID antenna 16 are present at a local density high enough to form a conductive path throughout the RFID antenna 16 structure. The conductance results from the contact between the conductive particles 340 that are present at levels sufficient to form a network within the mixture of both conductive 340 and non-conductive 330 particles. After dispersal due to ingestion, the conductive network is destroyed and the structure no longer effectively functions as an RFID antenna 16.

Typically, non-conductive 330 particles are medicines in particle form, so some additional treatment is necessary to create an appropriate mixture that forms a conductive path and a functional RFID antenna 16. One method for creating this conductive structure is to mix conductive particles 340, such as small metallic particles, with the non-conductive medicine particles 330 at an appropriate ratio to produce a conductive mixture. Conductive particles 340 may be metallic, such as small gold particles, or small conductive particles such as those made from conducting polymers such as polythiophene, and the like. Additionally, conductive coatings may be formed on the non-conductive particles 330 to create conductive particles 340, as the formation of a conductive network only requires surface conductivity due to the point-to-point aspect of the conducting network.

Figure 19:
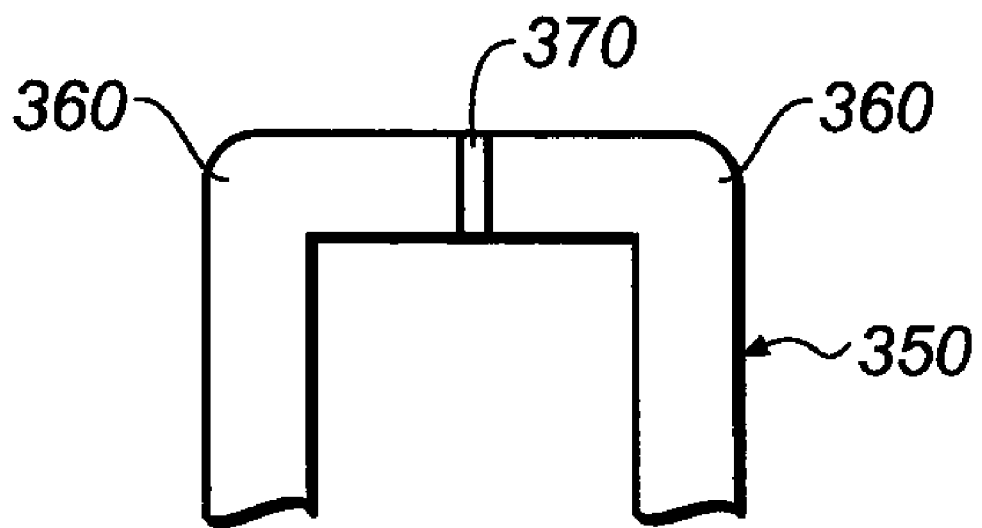
FIG. 19 is an expanded view illustration of an alternative RFID antenna segment of a fragile RFID tag whose resonance characteristics change due to breakdown in an antenna designed to be fragile.

FIG. 19 is an expanded view illustration of an alternative RFID antenna segment of a fragile RFID tag whose resonance characteristics change due to breakdown in an antenna designed to be fragile. In this case, the RFID antenna 16 is comprised of both conductive segments 360 and binding segment 370. Fragility of the structure results from the dissolution of the binding segment 370 when digestion occurs. The binding segment 370 may play a number of possible roles in the establishment of a conductive bridge between the conductive segments 360. In one embodiment the binding segment 370 is made of a conductive material that causes a conductive path to exits between the conductive segments 360. Alternatively, binding segment 370 is made of a simple material that holds two pre-stressed conductive segments 360 in intimate contact, establishing a conductive path in the RFID antenna 16. In this latter case, binding segment 370 must dissolve when ingested and release the pre-stressed conductive segments causing the conductive path to be broken.

The invention has been described in detail with particular reference to certain preferred embodiments thereof, but it will be understood that variations and modifications can be effected within the scope of the invention.

PARTS LIST 3 broadcast signal
4 person/subject
5 medical kiosk
10 RFID tag
12 circuit
14 resonant cavity
15 kiosk computer
16 RFID antenna
17 kiosk proximity detector
18 substrate
19 home computer
20 container for medicine
21 medicine
22 tagged medicine with fragile RFID
25 earpiece and boom
30 monitoring device
32 storage device
35 emitter
36, 36a transceiver
38 monitor support
40 monitor "off" state
42 computer
44 monitor
45 tagged medicine dispenser
47 change state loop
50 monitor activation
52 collar
53 lanyard
54 belt
55 change of state of monitor
56 handheld device
57 medicine dispenser
58 overhead apparatus
59 wall mount apparatus
60 monitor time-out
65 monitor off
70 end-data signal
75 detect tag
80 read and combine data
85 store data decision
90 transmit data decision
95 process data decision
100 transmit data
105 task completion
110 monitor "off" check after task
115 display results
120 store data
125 process data
130 end state
135 time check
140 patient history
145 correct medication time
150 determine to take/not take medication
155 take medication
160 sensor location
165 identify environmental conditions
170 patient history comparison
175 identify wrong medication or dosage
180 identify environment for drug
185 identify time for medication
190 identify wrong combination of medications
200 RFID tagged capsule
210 three-dimensional coil
220 compound capsule
230 tag that breaks down due to mechanical wear
240 bone surface tag
241 RF blocking layer
250 power source
260 reactive compound connector
270 external acoustical stimulation tag
280 tuning fork
290 base of tuning fork
300 embedded tag
310 cube-corner material
320 quantum dots
330 non-conductive particle
340 conductive particle
350 RFID antenna segment
360 conductive segment
370 binding segment

The invention claimed is:

1. A method for monitoring ingestion of medicine comprising the steps of:
   forming an antenna comprised of conductive material and said medicine;
   forming a digestible radio frequency identification (RFID) tag comprised of at least one of said antennas;
   ingesting said RFID tag;
   activating said RFID tag with signals and power from an external transmitter;
   transmitting signals from said RFID tag to an external receiver; and
   monitoring a signal from said RFID tag for changes in said signal due to dissolution of said antenna;
   wherein said conductive material comprises metal segments and said medicine binds together said segments of said antenna.

2. A method as in claim 1 wherein said segments are pre-stressed, whereby said segments are released upon dissolution of said antenna.

3. A medication for administration by mouth, comprising:
   an antenna comprising said medication and conductive material; and
   an RFID tag connected to said antenna,
   whereby dissolution of said medication renders said antenna inoperable;
   wherein said conductive material comprises conductive segments bound in contact by said medication.

4. A medication as in claim 3, wherein said segments are pre-stressed, whereby said segments are released upon dissolution of said medication.

* * * * *